(12) United States Patent
Nandy

(10) Patent No.: US 8,310,531 B2
(45) Date of Patent: Nov. 13, 2012

(54) METHODS AND APPARATUSES FOR PROCESSING FLUORESCENCE IMAGES

(75) Inventor: Shiddharta Nandy, Tyne and Wear (GB)

(73) Assignee: Genetix Corporation, San Jose, CA (US)

( * ) Notice: Subject to any disclaimer, the term of this patent is extended or adjusted under 35 U.S.C. 154(b) by 482 days.

(21) Appl. No.: 12/534,387

(22) Filed: Aug. 3, 2009

(65) Prior Publication Data

US 2011/0025880 A1 Feb. 3, 2011

(51) Int. Cl.
*H04N 9/47* (2006.01)
*H04N 9/73* (2006.01)

(52) U.S. Cl. ......... 348/79; 348/226.1; 348/80; 382/128; 382/254; 382/276; 359/385

(58) Field of Classification Search ............ 348/79, 348/80, 226.1; 382/128, 254–390; 359/385–390
See application file for complete search history.

(56) References Cited

U.S. PATENT DOCUMENTS

| | | | | |
|---|---|---|---|---|
| 7,092,559 | B2 * | 8/2006 | Soussaline et al. | 382/133 |
| 7,141,429 | B2 * | 11/2006 | Munson et al. | 436/53 |
| 7,372,985 | B2 * | 5/2008 | So et al. | 382/133 |
| 7,379,578 | B2 * | 5/2008 | Soussaline et al. | 382/133 |
| 7,724,937 | B2 * | 5/2010 | So et al. | 382/133 |
| 7,869,011 | B2 * | 1/2011 | Christensen et al. | 356/72 |
| 7,871,164 | B2 * | 1/2011 | Luther et al. | 351/205 |
| 2003/0102214 | A1 * | 6/2003 | Munson et al. | 204/450 |
| 2003/0167130 | A1 * | 9/2003 | Soussaline et al. | 702/19 |
| 2005/0036667 | A1 * | 2/2005 | So et al. | 382/128 |
| 2006/0127369 | A1 * | 6/2006 | Christensen et al. | 424/93.7 |
| 2006/0196771 | A1 * | 9/2006 | Munson et al. | 204/451 |
| 2006/0206482 | A1 * | 9/2006 | Soussaline et al. | 707/6 |
| 2006/0257013 | A1 | 11/2006 | Ramm | |
| 2007/0047071 | A1 * | 3/2007 | Honda et al. | 359/368 |
| 2007/0167842 | A1 * | 7/2007 | Tanikawa et al. | 600/476 |
| 2007/0243545 | A1 | 10/2007 | Kilpatrick | |

(Continued)

FOREIGN PATENT DOCUMENTS

WO WO 2008/019299 A2 2/2008

OTHER PUBLICATIONS

Mertens, Tom et al.; "Exposure Fusion"; 9 pages, May 2009.

(Continued)

*Primary Examiner* — Haresh N Patel
(74) *Attorney, Agent, or Firm* — Kilpatrick Townsend & Stockton LLP

(57) ABSTRACT

A method for generating a fluorescence microscopy image of a sample. The method comprises a step of obtaining a series of fluorescence microscopy images of the sample for a plurality of different focal plane depths in the sample and different exposure times. The images may be obtained directly from a microscope, or from a library of images. Images comprising the series of fluorescence microscopy images are combined to form a single resultant fluorescence microscopy image of the sample. The single resultant image may then be analyzed as if it were a conventional fluorescence microscopy image, e.g. by visual inspection or numerical processing. However, because the resultant image is based on images from a range of focal plane depths and exposure times, different structures that appear under only certain conditions (i.e. in only certain ones of the original series of fluorescence microscopy images) can appear together in a single image, thus simplifying visualization, interpretation and analysis of the sample.

13 Claims, 8 Drawing Sheets

U.S. PATENT DOCUMENTS

| | | | |
|---|---|---|---|
| 2008/0212172 A1 | 9/2008 | Zhu et al. | |
| 2008/0212866 A1 | 9/2008 | Lett | |
| 2009/0025489 A1* | 1/2009 | Christensen et al. | 73/864 |
| 2009/0072171 A1* | 3/2009 | So et al. | 250/584 |
| 2009/0257024 A1* | 10/2009 | Luther et al. | 351/206 |
| 2010/0158333 A1* | 6/2010 | Henkelman et al. | 382/131 |
| 2010/0224796 A1* | 9/2010 | Mertz et al. | 250/459.1 |
| 2011/0084218 A1* | 4/2011 | Duhr et al. | 250/459.1 |
| 2011/0090500 A1* | 4/2011 | Hu et al. | 356/337 |
| 2011/0275932 A1* | 11/2011 | Leblond et al. | 600/425 |

OTHER PUBLICATIONS

Rantanen, Ville; "Work No. 1: Fluorescence imaging, oil objectives, and tissue sample"; 6 pages, May 2009.

Zeiss, Carl; "Inside4D: Live is live. Now"; 2002, 4 pages, May 2009.

"Z-Stack: Digital Imaging"; http://www.zeiss.com/C12567BE0045ACF1/allBySubject/6A9B2F1F9EC90DFAC12 . . . , 1 page, May 2009.

"HDRI—High Dynamic Range Image Acquisition"; http://www.zeiss.de/C12567BE0045ACF1/allBySubject/D21B3D404FA023A7C1257 . . . , 2 pages, May 2009.

"From Images to Answers: Advanced Fluorescence Acquisition (AFA): Manage Complex Acquisition Modes and Image Sets An Image-Pro Plug-In Module"; 2004, 2 pages.

"Morphological spot couting from stacked images for autmoated analysis of gene copy numbers by flourescence in situ hybridization" (GRIGORYAN) Journal of Biomedical Optics, Jan. 2002, vol. 7, No. 1, pp. 109-122, XP008102322.

* cited by examiner

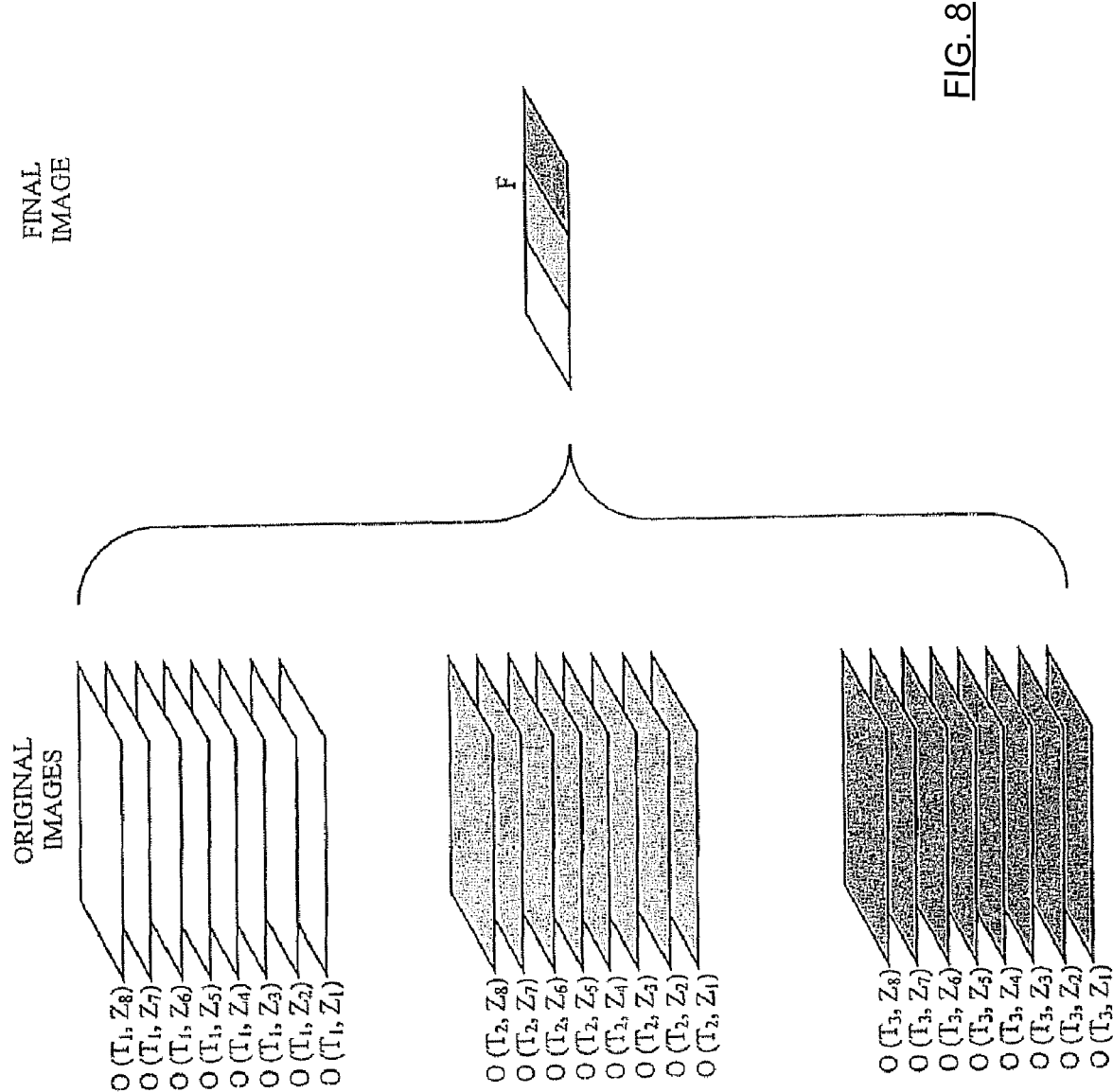

METHODS AND APPARATUSES FOR PROCESSING FLUORESCENCE IMAGES

BACKGROUND

The invention relates to fluorescence imaging, and in particular to obtaining and processing fluorescence images, e.g. fluorescence microscopy images.

Fluorescence microscopy is a valuable research and diagnostic tool. One particular type of fluorescence microscopy is the so-called FISH (fluorescence in-situ hybridization) technique. The FISH technique is a well known technique used to detect and localize the presence or absence of specific DNA sequences on chromosomes (which may be referred to as "targets"). The technique relies on the use of fluorescent marker probes designed to bind to target DNA sequences. A specimen to be examined for the target sequence is exposed to the probe material so that molecules comprising the probe bind to target DNA in the specimen (if any). The specimen, which is typically a sample on a slide, is then viewed with a fluorescence microscope to identify regions of the sample which fluoresce due to the presence of the bound fluorescent probe. Fluorescent regions in a fluorescence image correspond with regions containing the target DNA. FISH techniques can also be used to detect and localize specific mRNAs within tissue samples, e.g. to help define spatial-temporal patterns of gene expression within cells and tissues.

Fluorescence microscopy is often practiced as a digital microscopy technique. That it to say, a fluorescence microscope will be used to record a digital image of a sample. The image may then be stored and later retrieved for analysis, e.g., by viewing on a general purpose computer running appropriate software, or on a dedicated monitor associated with the fluorescence microscope itself. The general principles of digital fluorescence microscopy and the obtaining of digital fluorescent microscopy images are well understood and are not describe further here.

Once a digital fluorescence microscopy image has been obtained, it will be analyzed. This may involve a user viewing the image and making a clinical assessment, e.g. to determine if the image displays a pattern of fluorescence that indicates a particular condition, e.g. based on the identified presence/distribution of the target DNA to which the fluorescent molecule (fluorophore) has bound. Alternatively, or in addition, the digital fluorescence microscopy image may be analyzed using digital image processing techniques. For example, the image may be automatically processed to count the number of spots of fluorescence (bright spots) in the image using numerical processing techniques. Automated image processing techniques can provide a higher throughput of analyzed images that would typically be the case if each image is manually inspected/analyzed.

A drawback of digital fluorescence microscopy is that fluorescence images are often unable to represent all of the available information about the distribution of a fluorophore probe in the sample, e.g. a microscope's optics will often not have a large enough depth of field for all spots (fluorescent structures) to be in focus in a single image. Furthermore, it is often the case that the level of fluorescence associated with the presence of the target DNA varies across an image, even for a uniform distribution of target DNA. Images can also be affected by background light and non-specific auto-fluorescence which can reduce the contrast of target DNA marked with the fluorescent probe in the image.

These drawbacks mean that distinguishing and identifying target structures (e.g. fluorophore-labeled DNA in the FISH technique) can be problematic, both for humans and for automatic image processing systems/algorithms. These problems can be exacerbated for specimens containing material from different types of tissue, e.g. lung or prostate, such as may be found in a TMA (tissue micro-array) slide. This is because different tissue-types can absorb the fluorescent probe dyes differently. This means a typical spot-counting task can become difficult because the fluorescence intensity of spots in some tissue types can be very different from the fluorescence intensity of spots in other tissue types because of the different affinities of the two tissue types to the fluorophore probe. For example, spots in one type of tissue might be very bright whilst corresponding spots in another tissue type might be almost invisible. Another factor which can affect staining intensity is specimen thickness. This can lead to variations in fluorophore-labeled spot intensity (and other structures) in fluorescent microscopy images, even for a single tissue type with a uniform distribution of the target of interest.

There is therefore a need for schemes for obtaining and processing fluorescent microscopy images which are less affected by the above-mentioned drawbacks.

SUMMARY

According to a first aspect of the invention there is provided a method for generating a fluorescence image of a sample for analysis, the method comprising the steps of: (a) obtaining fluorescence images, e.g. fluorescent microscopy images, of the sample for a plurality of different focal plane depths in the sample and different exposure times, wherein the respective fluorescence images each comprise image signal values for an array of common pixel locations; and (b) combining the image signal values for the fluorescence images from the different focal plane depths and different exposure times to form a resultant fluorescence image of the sample.

The image may be analyzed to determine whether the corresponding sample is associated with a specific biological condition, for example. In this regard the resultant fluorescence image may be treated as if it were a conventional fluorescence image and may be used to determine if it is associated with a sample having a particular biological condition in the same was as conventional fluorescence images are used.

As is conventional, the images will in general be represented by data sets, e.g. according to any known image-data format. Thus in accordance with embodiments of the invention, an input dataset representing images of the sample for a plurality of different focal plane depths in the sample and different exposure times is transformed into an output data set representing a resultant fluorescence image of the sample. The method may operate on an apparatus such as a suitably configured special purpose computer, or a general purpose computer programmed with particular software for implementing the method. Software for implementing the method may be stored on a computer-readable storage medium in accordance with embodiments of the invention.

Thus a single fluorescence image may be provided which can then be analyzed further, e.g. according to conventional analysis schemes for fluorescence images. The single resultant fluorescence image is generated from a combination of images from different focal plane depths in a sample and for different exposure times. The inventors have found that processing in accordance with embodiments of the invention can help in automatically obtaining good quality images which capture the important fluorescent structures in a sample even in the presence of non-uniform fluorescence, background fluorescence and auto fluorescence. Thus the final image may be generated as a collocation of the "best" aspects (e.g. the structures that are in best focus and best exposed) from each of the original images, thus capturing all the important structures in good focus and clearly exposed. Subsequent analysis of the single final image is not only faster than an otherwise separate analysis of multiple images, but there can also be a reduced scope for misinterpretation. For example, there is reduced risk of double counting fluorescent spots which appear in multiple ones of the original images since the spots will generally appear as a single feature in the final resulting image. Furthermore, embodiments of the invention provide schemes which have been found to automatically generate good quality images capturing the important fluorescent structures in a sample in the presence of non-uniform fluorescence, background fluorescence and auto fluorescence.

Thus embodiments of the invention may be used to produce a single image of a fluorescence probe signal in a sample which combines lightly and strongly stained cells together, while helping to avoid over- or under-exposing either, and which also incorporates fluorescence probe signals from different depths in a sample. The approach may be particularly suitable for imaging TMA slides, for example, where the tissue samples may come from different tissue types or patients and so be prone to displaying a wide range of fluorescent staining characteristics. The approach may also be particularly suitable for imaging large-section tissue samples where staining intensity can vary over a sample.

There are many ways the images could be combined. For example, combining the image signal values (e.g. image intensity values) for the fluorescence images from the different focal plane depths and different exposure times might comprise determining for each pixel location a weighted average of the corresponding image signal values in the different images for that location, wherein the weightings for each image signal value are based on a measure of a variation in image signal values among neighboring pixel locations (i.e. a characteristic measure of local contrast). In other examples, this step might comprise determining for each pixel location an image signal value from one of the images from the different focal plane depths and exposure times to be used for that pixel location in the single resultant image.

The combining of images may be performed in two stages. For example, the combining may comprise the steps of: (b1) deriving an intermediate image for each of the different exposure times from the images for the different focal plane depths for the respective different exposure times, and (b2) combining the resulting intermediate images for the different exposure times to form the single resultant image.

The step of deriving the intermediate images can be done in various ways.

For example, the intermediate images might be derived by selecting, for each of the different exposure times, one of the images from the different focal plane depths to be the derived intermediate image for that exposure time. The selection of the image as the derived intermediate image could be based, for example, on a quality-of-focus measurement for the different images. The quality-of-focus measurement may, for example, be based on a measure of variations in image signal value among pixels in the respective images, e.g. a summary measure of local contrasts across the whole image.

In another embodiment the intermediate images might be derived by performing a maximum intensity projection analysis of the images for the different focal plane depths for each of the respective exposure times.

In some cases the step of deriving the intermediate images might comprise selecting, for each of the different exposure times, a subset of the images from the different focal plane depths for that exposure time, and deriving the intermediate image for each exposure time by combining the corresponding subset of the images. The subset of the images may, for example, be based on a quality-of-focus measurement for the images at the different focal plane depths. Such a quality-of-focus measurement may be based on a measure of variations in image signal value among pixels in the respective images, for example.

The intermediate images may be derived from the subset of images for each exposure time in various ways. For example, the intermediate image for each of the different exposure times may be derived by performing a maximum intensity projection analysis of the respective subsets of the images.

The intermediate images may similarly be combined in various ways to form the final image. For example, combining the intermediate images might comprise determining for each pixel location in the intermediate images a weighted average of the corresponding image signal values in the different intermediate images, wherein the weightings for each image signal value in the intermediate images are based on a measure of a variation in the image signal values among neighboring pixel locations.

The final image generated in accordance with embodiments of the invention may be analyzed/measured according to any known techniques, for example, by visual inspection through a step of displaying the resulting fluorescence image on a monitor, and/or by numerical image processing.

Thus the single resultant fluorescence image of the sample may be presented to a user as a graphic display with image pixels of the graphic display displayed with a characteristic (e.g. brightness/color) based on parameters associated with the single resultant fluorescence image of the sample at corresponding pixel locations. Alternatively, or in a addition, the single resultant fluorescence image of the sample may be provided by way of a data structure, e.g. in a conventional image format, stored in a memory such that a user may subsequently access/retrieve data representing the single resultant fluorescence image of the sample from the memory for display and/or further analysis.

According to another aspect of the invention there is provided an apparatus for generating a fluorescence image of a sample for analysis comprising a source of fluorescence images of the sample obtained for a plurality of different focal plane depths in the sample and different exposure times, the respective fluorescence images comprising image signal values for a common array of pixel locations; the apparatus further comprising a processor operable to combine the image signal values for the fluorescence images from the different focal plane depths and different exposure times to form a single resultant fluorescence image of the sample.

BRIEF DESCRIPTION OF THE DRAWINGS

For a better understanding of the invention and to show how the same may be carried into effect reference is now made by way of example to the accompanying drawings in which:

FIG. 8 is a schematic pictorial representation of the processing of the flow diagram of FIG. 7;

DETAILED DESCRIPTION

Figure 1:
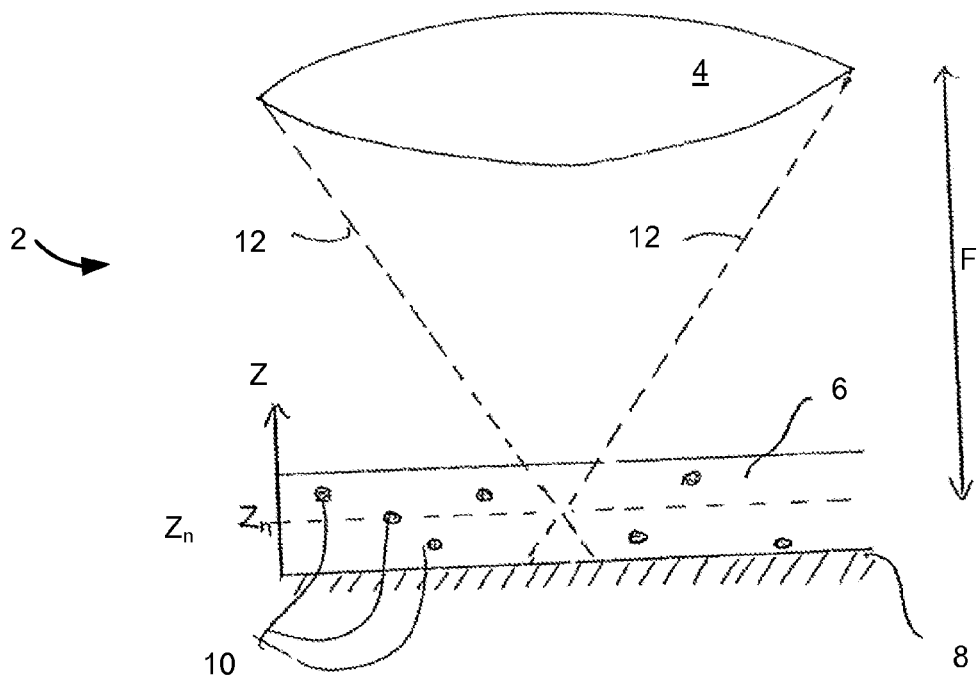
FIG. 1 schematically shows aspects of a digital fluorescence microscope for obtaining digital fluorescence microscopy images for processing in accordance with an embodiment of the invention.

FIG. 1 schematically shows aspects of a conventional digital fluorescence microscopy system 2 which may be used in accordance with embodiments of the invention. The system 2 comprises a digital fluorescence microscope 4 (schematically represented here as a simple lens) which is arranged to record fluorescence images of a sample 6 mounted on a slide 8. The sample 6 in this example is a conventional FISH-technique stained sample. Thus the sample is schematically shown in FIG. 1 to include various fluorescent spots 10 associated with regions where a fluorophore has become bound to a target DNA strand of interest for the application at hand (the specific biological application is not significant). Processing in accordance with embodiments of the invention may in general be applied to any biological sample which may be viewed using a digital fluorescence imaging system. The process of recording individual digital fluorescence images using the digital fluorescence microscopy system of FIG. 1 may be performed in broadly conventional manner.

Each digital image recorded by the microscopy system 2 comprises data representing image signal values for an array of pixel locations that map to spatial locations in a plane perpendicular to a viewing axis of the microscope 2 (i.e. a horizontal plane for the orientation shown in FIG. 1). Generally speaking a digital fluorescence microscopy system 2 will have a depth of focus which is shorter than the thickness of a sample under study. For example, a tissue specimen in a typical application may have thickness of around 4 microns which, when imaged at some magnifications, e.g. 40×, may be greater than the microscope objective's depth of field. The focus of the microscope 4 is schematically shown in FIG. 1 by the convergence of the dashed lines 12 representing paths for light rays. For the configuration shown in FIG. 1, the system is arranged to provide images for a focal plane depth that is approximately half-way through the sample 6 (as schematically indicated by the horizontal dashed line). This means some of the fluorescent spots 10 (e.g. the one which is second from the left in FIG. 1) will be in good focus in an image recorded for this configuration, whereas other spots, e.g. the right-most one in FIG. 1, will be in poor focus because they are not so close to the focal plane of the microscope. Thus it can be difficult to identify all fluorescent spots in a sample from a single image.

The position of the focal plane for the microscope 4 may be specified by a z-coordinate measured along the viewing axis of the microscope, i.e. measured vertically for the orientation shown in FIG. 1. The upper surface of the mounting slide 8 may arbitrarily be used for the origin (i.e. for Z=0). In FIG. 1 the focal plane is shown a depth $Z=Z_n$. As is conventional, the focal plane depth for which an image is to be recorded may be readily changed, e.g. by moving the microscope 4, or a component of it, relative to the slide 8. Thus a series of digital fluorescence microscopy images of the sample 6 may be recorded for different focal plane positions within the sample 6. Such a series may be referred to as a Z-stack of images, or simply a Z-stack.

Figure 2:
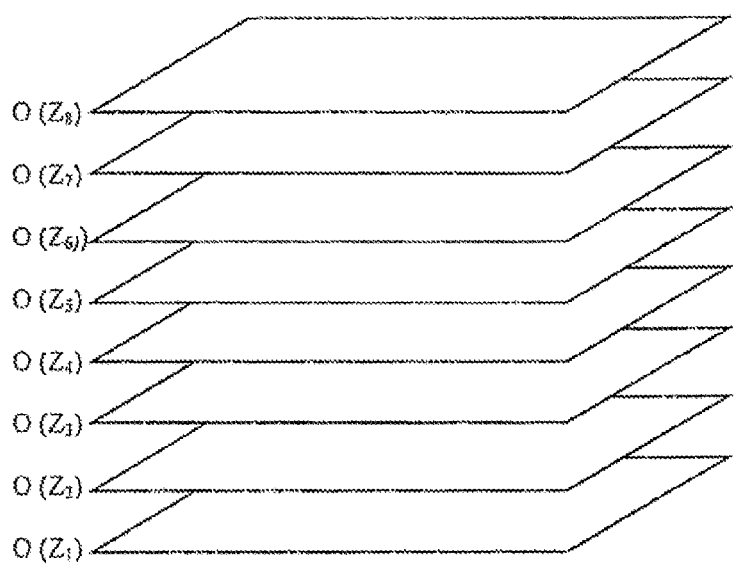
FIG. 2 schematically represents a stack of digital fluorescence microscopy images obtained for different focal plane depths in a specimen.

FIG. 2 schematically shows a Z-stack of images of the sample 6 of FIG. 1 obtained at different focal plane depths (i.e. different positions of the focal plane along the viewing axis of the microscope, that is to say an axis which is perpendicular to the microscope's focal plane). The Z-stack of FIG. 2 comprises eight images $O(Z_{1-8})$ corresponding to conventional digital microscopy images taken for eight different focal plane depths $Z_{1-8}$. The range of focal plane positions $Z_{1-8}$ span the approximate thickness of the sample 6. Thus by obtaining images for different focal plane depths in this way, it may be expected that fluorescent spots at different depths will appear in focus in at least one of the images of the Z-stack so that all spots can be properly identified in at least one image.

A conventional digital fluorescence microscope is also able to record images for different exposure times. Automatic exposure-time calculation techniques are often used to select an appropriate exposure time. However, these techniques can suffer from a problem in that excessive auto-fluorescence and background fluorescence can skew the exposure-time calculations such that overly-short exposure times are used. These can result in dark, low contrast images. Furthermore, in some situations there can be a relatively wide range of fluorescent activity in a stained sample, e.g. because of different tissue affinities to the fluorescent stain, or wide variations in the density of the target structure of interest in the sample. This means some fluorescent regions in a sample can appear over-exposed in an image, while some other areas can appear under-exposed. This is because an exposure time that works well for imaging one area of the sample may over- or under-expose another area. Thus to obtain a good digital fluorescence microscopy image, careful consideration of the exposure time required is needed.

The present inventors have appreciated this need to carefully consider different focal plane depths and exposure times in digital fluorescence microscopy impacts the efficacy and efficiency of these analysis schemes. This is because the need to analyze multiple different images of a single sample, whether by automated numerical processing or by visual inspection, reduces the rate at which samples can be processed. However, if fewer images are obtained to reduce the analysis time, there is an increased risk of details of the fluorophore-tagged target structures being lost, e.g. through a lack of spatial focus, or through under- or over-exposure. For example, a typical FISH cytological analysis may be based on "spot counting" of fluorescent markers in the fluorescent microscopy images. To do this accurately, cell outlines should be readily distinguishable from the background in the DAPI (counterstain) image and the spots (i.e. the fluorescent probe signals) should be readily distinguishable from cells and other structures in the FISH images. This can be difficult where fluorescent structures are not readily and clearly identifiable.

Figure 3:
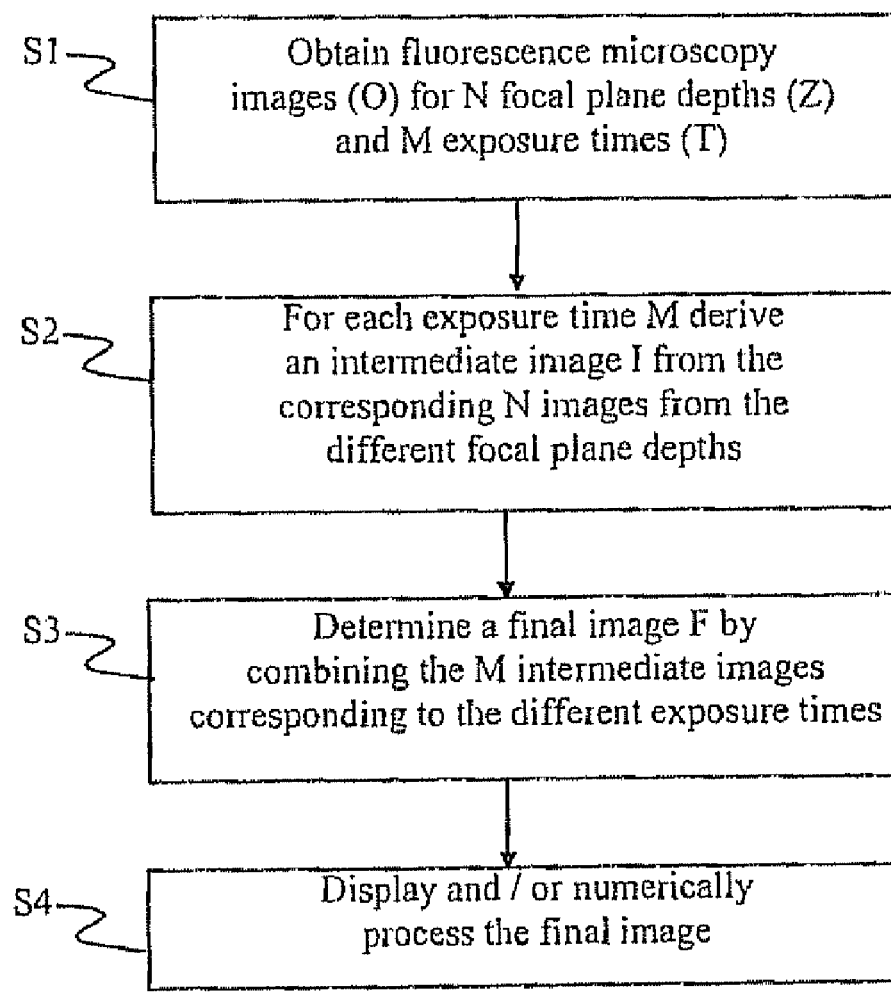
FIG. 3 is a flow diagram representing a scheme for combining digital fluorescence microscopy images obtained for a plurality of different exposure times and different focal plane depths to generate a single resultant image according to an embodiment of the invention.
Figure 4:
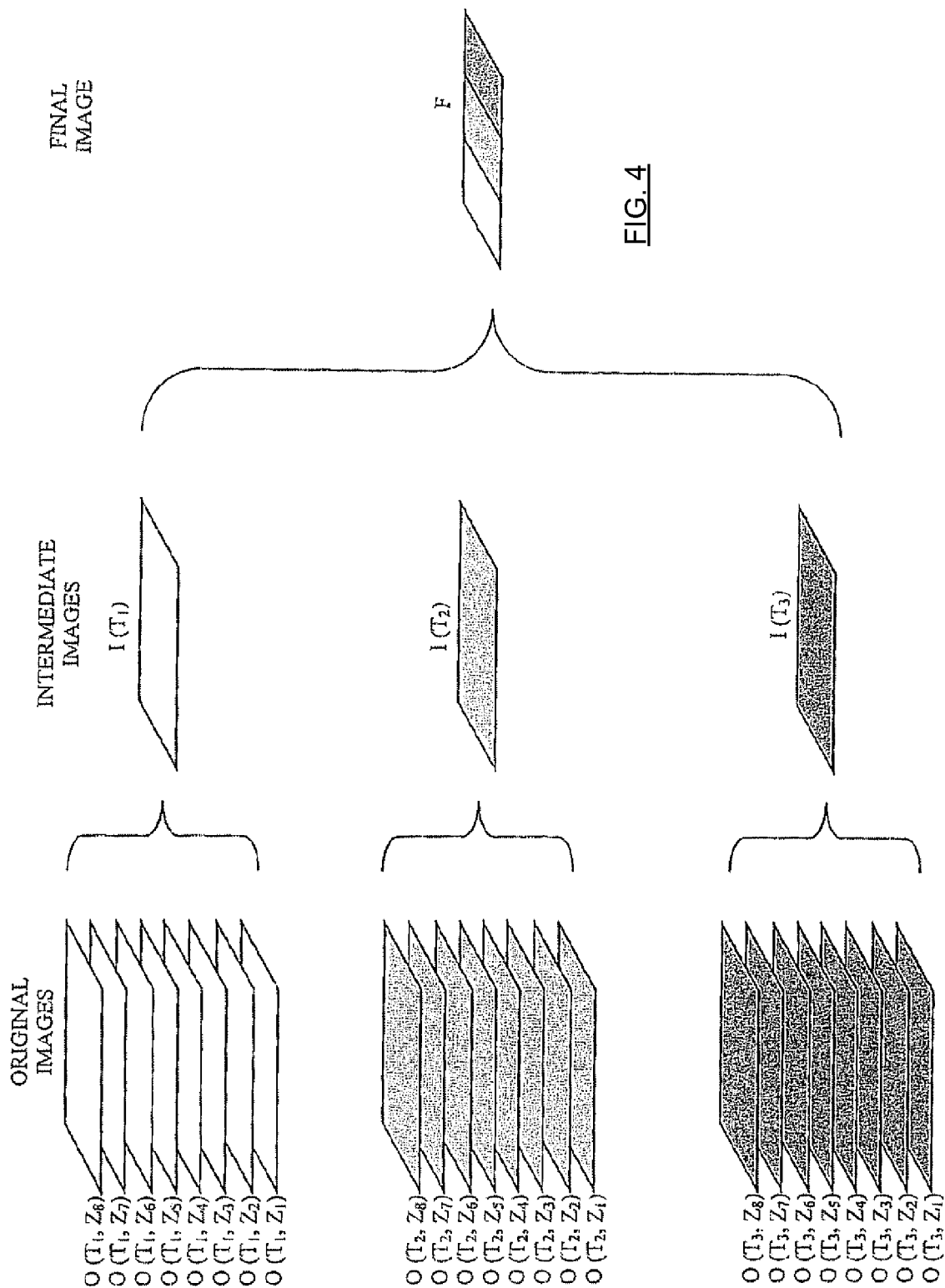
FIG. 4 is a schematic pictorial representation of the processing of the flow diagram of FIG. 3.

FIG. 3 is flow diagram schematically representing a method for generating a fluorescence microscopy image of a sample for subsequent analysis (e.g. by numerical processing or visual inspection) according to an embodiment of the invention. FIG. 4 is a highly schematic figure representing how different fluorescence microscopy images are obtained and combined in accordance with the method of processing shown in FIG. 3.

In Step S1 a series of digital fluorescence microscopy images O of the sample are obtained using a conventional digital fluorescence microscope. Images O are obtained for N different focal plane depths ($Z_{1-N}$) in the sample and for M different exposure times ($T_{1-M}$) at each depth.

The number of images suitable for a given implementation may, for example, be based on considerations such as the sample thickness, microscope depth of focus, expected dynamic range of fluorescence signals, and empirical observations of "test" samples.

For example, for a microscope having a depth of acceptable focus spanning a distance S, and a sample having a thickness A, each Z-stack might comprise a series of A/S images offset from one another in steps of S so that all parts of the sample appear in acceptable focus in at least one image. Appropriate exposure times may be based on experimentation. For example, one might use what is considered to be a "typical" sample for the application at hand, and apply conventional automatic exposure determination techniques to a bright area of the sample and a dark area of the sample to give a measure of appropriate exposure times for the two extremes of the typical dynamic range. Images may then be obtained for other samples using these two exposure times, or perhaps these two exposure times and one or more other times in between. In another example, conventional automatic exposure determination techniques may be applied to a dark area of a typical sample. Images may then be obtained for other samples using this exposure time and one or more multiples thereof, e.g. twice the exposure time, or two- and three-times the exposure time. It will be appreciated that one way of obtaining multiple exposure times, e.g. of say 300 ms and 600 ms, would be to obtain two separate 300 ms exposures and treat one as the desired 300 ms image, and sum them together to provide the desired 600 ms image. This would reduce the overall time required to obtain the multiple images.

Returning now to Step S1 of FIG. 3, the series of images O thus comprises a number of (i.e. M) Z-stacks, wherein each Z-stack is recorded using a different exposure time. Accordingly, a total of (N×M) images are obtained. These are all conventional digital fluorescence microscopy images, and may sometimes be referred to here as "original" images. In this example, the original images are recorded for eight different focal plane depths ($Z_{1,2\ldots 8}$), and for three different exposure times ($T_{1,2,3}$) at each depth. There are therefore a total of 24 original images, and these may be identified by respective labels O($T_{1,2,3},Z_{1,2\ldots 8}$), as schematically shown at the left of FIG. 4 under the general heading "ORIGINAL IMAGES". In FIG. 4 the different exposure times are schematically represented by different levels of shading. Each of the original images comprises image signal values for an array of common pixel locations. Corresponding pixel locations in the different images map to the same horizontal position on the sample (i.e. a given volume of the sample projects to the same pixel location(s) in each image).

It will be appreciated that while Step S1 is described here in the context of obtaining images directly from a digital fluorescence microscope, in other examples the images may be obtaining from a database of previously recorded images.

In Step S2, a plurality of intermediate images I are derived. An intermediate image is derived from the N images comprising each Z-stack. Thus in this example three intermediate images are derived from respective ones of the three groups of original images O($T_1,Z_{1,2\ldots 8}$), O($T_2,Z_{1,2\ldots 8}$) and O($T_3,Z_{1,2\ldots 8}$) associated with the three exposure times. The intermediate images I may thus be identified by the exposure time T with which they are associated. Thus the intermediate images are shown in FIG. 4 with respective labels I($T_1$), I($T_2$) and I($T_3$) under the general heading "INTERMEDIATE IMAGES". There are various ways the intermediate images may be derived from their respective Z-stacks. In this example, the images for each Z-stack are processed to determine a parameter indicative of a how well focused the image is, i.e. a characteristic "quality-of-focus" measurement is determined for each image. This parameter may be based, for example, on a measure of the average variation in image signal values among neighboring pixels. For example, for each pixel location in each image, a measure of the variance of image signal values in a surrounding 3×3 square of pixels may be determined. These variance values may then be averaged across an image. Images with a relatively high average local variance in signal values thus have relatively high degrees of pixel-to-pixel contrast, which is indicative of good focus (i.e. less blurring).

In Step S2 the single image having the highest characteristic "quality-of-focus" measurement (i.e. the image deemed to be the best focus image) from the respective Z-stacks for each exposure time is taken to be the derived intermediate image for that exposure time. (It will be appreciated there are many other ways of defining an appropriate characteristic "quality-of-focus" measurement to be used in determining the "best focus" image for each Z-stack, e.g. in accordance with the well known general techniques of image processing.)

In Step S3, a final resultant image F is formed by combining the M intermediate images I($T_{1,2,3}$). The final resultant image is schematically shown in FIG. 4 with the label F under the general heading "FINAL IMAGE". The final image is represented in three shades of gray to indicate that it is formed from images taken with the different exposure times. In this example embodiment the combining ("image fusion") is based on calculating, for each pixel location, a weighted average of the signal values in the respective intermediate images. The weightings for each pixel in the different intermediate images are based on a local contrast measure for each pixel. Thus a characteristic local contrast measurement is made for each pixel in each of the intermediate images. This contrast parameter may be based, for example, on a measure of the difference between the maximum and minimum image signal values in a group of surrounding neighbor pixels. For example, for each pixel location in each intermediate image, a measure of the maximum difference in image signal values in a surrounding 3×3 square of pixels may be determined. (It will again be appreciated there are many other ways of defining an appropriate characteristic "contrast" measurement). Pixels having relatively high image signal value differences in their local neighborhood are associated with areas of high local contrast. High local contrast is generally indicative of an image in which structures are well-defined.

Thus the final image signal value for each pixel location in the final image is determined by averaging the image signal values in the intermediate images for the corresponding pixel locations, wherein the averaging is weighted by the local characteristic "contrast" measurement established for each pixel location. Image signal values from pixel locations associated with relatively high local contrast in the intermediate images are weighted more than image signal values from pixel locations associated with relatively low local contrast.

In Step S4, the final image from Step S3 is analyzed, e.g. by visual inspection or automated numerical processing. This analysis may be of any known type for analyzing digital fluorescence microscopy images. Thus in effect the single final image F provided by combining images from different focal plane depths in a sample and for different exposure times may be analyzed as if it were a single conventional unprocessed digital fluorescence microscopy image. However, the final image here may be seen as a collocation of images which combines the "best" aspects (i.e. the structures that are in best focus and best exposed) from each of the original images, thus capturing all the important structures in good focus and clearly exposed. Subsequent analysis of the single final image is not only faster than an otherwise separate analysis of multiple images, but there can also be a reduced scope for misinterpretation. For example, there is reduced risk of double counting fluorescent spots which appear in multiple ones of the original images since the spots will generally appear as a single feature in the final resulting image. Furthermore, embodiments of the invention provide schemes which have been found to automatically generate good quality images capturing the important fluorescent structures in a sample in the presence of non-uniform fluorescence, background fluorescence and auto fluorescence.

Subsequent analysis of the single final image is not only faster than an otherwise separate analysis of images, but is also reduced scope for misinterpretation, e.g. because there is reduced risk of double counting fluorescent spots appearing in multiple original images.

It will be appreciated that there are various modifications that could be made to the method described above with reference to FIGS. 3 and 4.

For example, whereas in the above example the single "best-focus" image is selected from the respective Z-stacks to derive the intermediate images for each exposure time, in an alternative embodiment the intermediate images for each exposure time may instead be based on a combination of the different images comprising the respective Z-stacks. For example, each pixel in a Z-stack could be assigned a contrast measure, e.g. in the same was as described above for the intermediate images in Step S3 of the flow diagram of FIG. 3. The intermediate image may then be formed by assigning an image signal value for each pixel location of the intermediate image which corresponds with the image signal value for that pixel location associated with the greatest contrast measurement in the different images making up the Z-stack. A potential advantage of this method over that described above is that it can be less effected by structures in the sample (e.g. cells) which are significantly inclined (sloped) relative to the focal plane of the microscope images. The single "best-focus" image approach described above will in general provide a "slice" through inclined structures and so result in an appearance that is less well matched to their true shape.

The inventors have found the particular approach described above with reference to FIGS. 3 and 4 is especially suited to generating a single final image for a DAPI counterstain slide.

Figure 5:
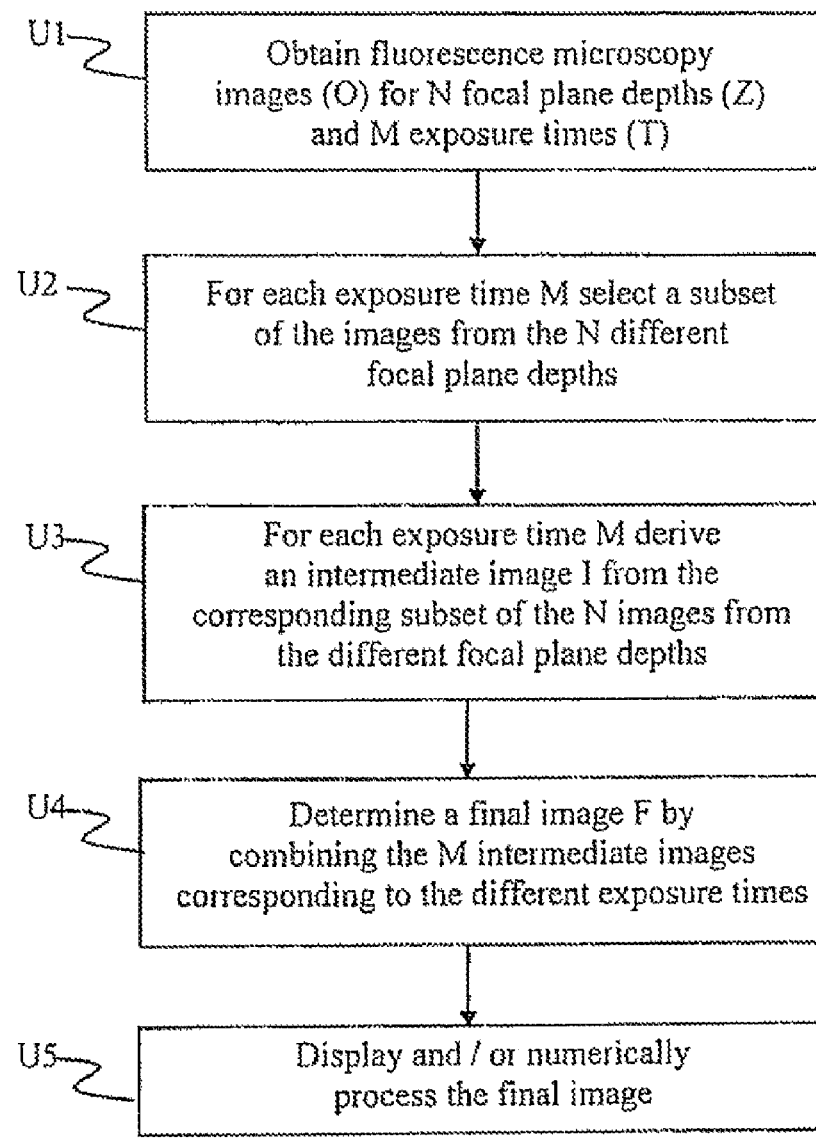
FIG. 5 is a flow diagram representing a scheme for combining digital fluorescence microscopy images obtained for a plurality of different exposure times and different focal plane depths to generate a single resultant image according to another embodiment of the invention.
Figure 6:
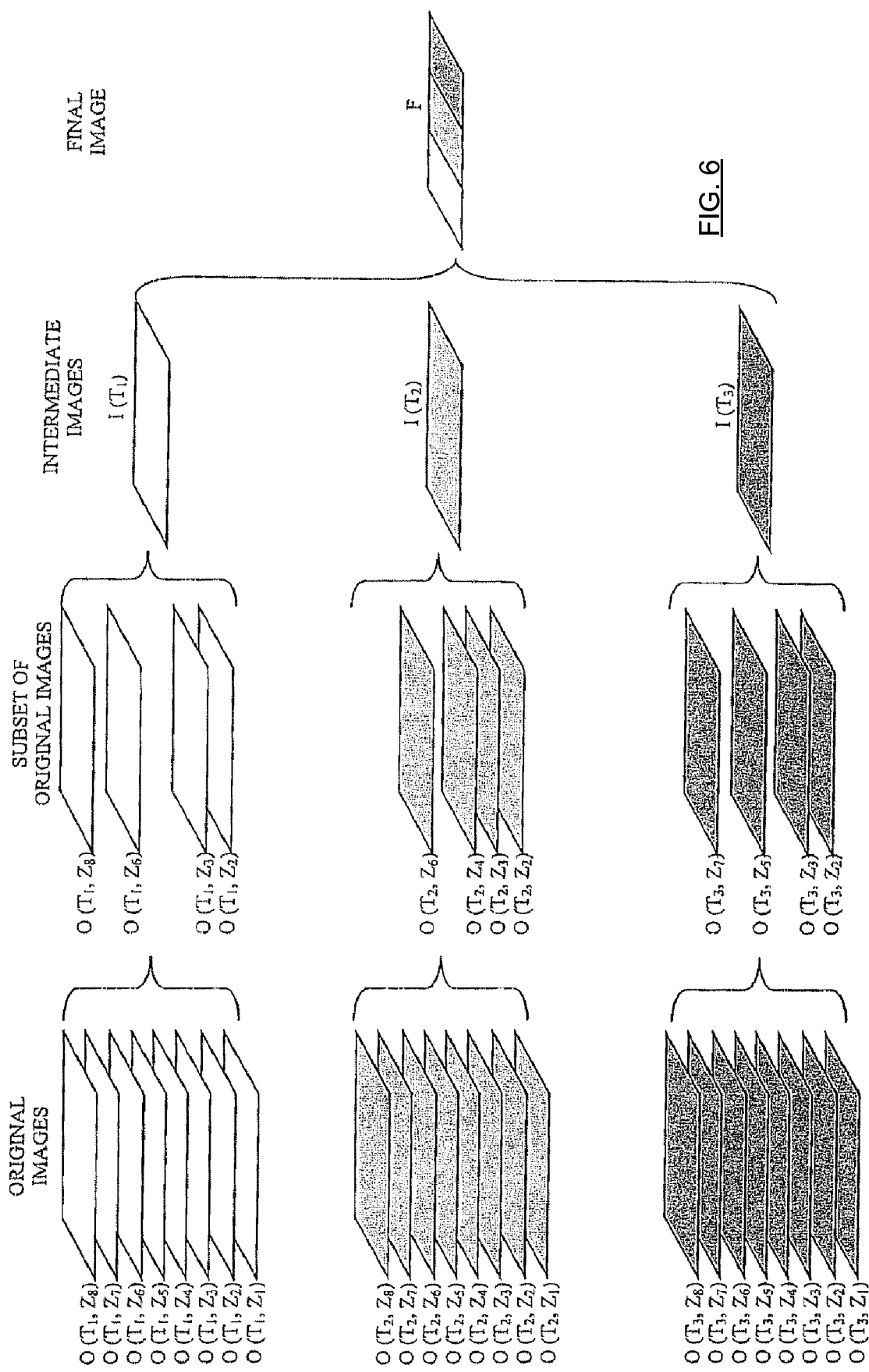
FIG. 6 is a schematic pictorial representation of the processing of the flow diagram of FIG. 5.

FIG. 5 is flow diagram schematically representing a method for generating a fluorescence microscopy image for subsequent analysis according to another embodiment of the invention. FIG. 6 is a highly schematic figure representing how different fluorescence microscopy images are obtained and combined in accordance with the method of processing shown in FIG. 5. FIGS. 5 and 6 broadly correspond to, and will be generally understood from, FIGS. 3 and 4. However, whereas FIGS. 3 and 4 relate to a scheme the inventors have found to be especially suited to generating a single final image for detecting a DAPI counterstain, FIGS. 5 and 6 relate to a scheme that the inventors have found to be especially suited to generating a single final image for detecting a FISH probe.

Step U1 of FIG. 5 is the same as Step S1 of FIG. 3 (although the actual sample and the staining used in preparing the sample may be different). Thus in Step U1 a series of digital fluorescence microscopy images O are obtained using a conventional digital fluorescence microscope. As in the example of FIG. 3, images are recorded for eight different focal plane depths ($Z_{1,2\ldots 8}$), and for three different exposure times ($T_{1,2,3}$) at each depth. There are therefore again a total of 24 original images which may be identified by respective labels $O(T_{1,2,3}, Z_{1,2\ldots 8})$, as schematically shown at the left of FIG. 6 under the general heading "ORIGINAL IMAGES". Again, it will be appreciated that while this step is described here in the context of obtaining images directly from a digital fluorescence microscope, in other examples the images may be obtaining from a database of previously recorded images.

In Step U2 a subset of the original images is selected for further analysis. Images within this subset may conveniently be referred to as the "selected images". The subset of selected images in this example comprises the images for each exposure time which are associated with a relatively high characteristic quality-of-focus measurement. For example, a characteristic quality-of-focus measurement may be determined for each image, such as described above in relation to Step S2 of FIG. 3. The subset of images for each exposure time might then be selected based on this parameter. I.e. the subset of images selected at step U2 may be the images from each exposure time which are considered as being most in focus. For example, the subset might comprise the 50% of images in each Z-stack associated with the highest quality of focus measurement. In another example, the subset for each exposure time might comprise all images in the corresponding Z-stack having a characteristic "quality-of-focus" measurement greater than a pre-defined threshold. In another example, the subset may comprise the images associated with focus measurements that are within a specified tolerance of the image in best focus for that exposure time, e.g. to select those images with focus measurements greater than half that of the best-focus plane.

It is assumed for this embodiment the subset is selected to comprise the 50% of images in each Z-stack associated with the highest value of focus measurements. This subset of images is schematically shown in FIG. 6 under the general heading "SUBSET OF ORIGINAL IMAGES". In this depicted example, the four best focus images for the Z-stack associated with exposure time T1 are assumed to be the images at the different focal plane depths of $Z_2$, $Z_3$, $Z_6$, and $Z_8$, as schematically shown in FIG. 6. In the general case the four best focus images for the Z-stacks associated with the other exposure times will not necessarily be at the same focal plane depths, e.g., such as schematically indicated in FIG. 6.

In Step U3, an intermediate images I is derived for each exposure time from the corresponding selected images. Step U3 is thus similar to S2 described above. However, whereas the intermediate images of Step S2 of FIG. 3 are derived from a consideration of all original images for the respective exposure times, the intermediate images of Step U3 of FIG. 5 are derived from a consideration of only the subset of images selected at Step U2 (i.e. the best focus images).

Thus in Step U3 an intermediate image is derived for each exposure time from the selected images from each Z-stack. Accordingly, in this example, three intermediate images are derived from respective ones of the three groups of selected images $O(T_1,Z_{2,3,6,8})$, $O(T_2,Z_{2,3,4,6})$ and $O(T_3,Z_{2,3,5,7})$. The intermediate images I may again be identified by the exposure time T with which they are associated. Thus the intermediate images are shown in FIG. 6 with respective labels $I(T_1)$, $I(T_2)$ and $I(T_3)$ under the general heading "INTERMEDIATE IMAGES".

There are various ways the intermediate images may be derived from the selected images for each Z-stack. In this example, a maximum intensity projection (MIP) is used to collapse the stack of selected images for each exposure time to a single intermediate image. As is well known, a MIP is performed by selecting, for each pixel location, the greatest image signal value for that pixel location from the selected images.

In Step U4 of FIG. 5, a final resultant image F is formed by combining the M intermediate images $I(T_{1,2,3})$ from Step U3. The final resultant image is schematically shown in FIG. 6 with the label F under the general heading "FINAL IMAGE". As in FIG. 4, the final image in FIG. 6 is again represented in three shades of gray to indicate that it includes data derived from images taken with different exposure times. In this example embodiment the combining/image fusion of Step U4 is based on the same method as described above for Step S3 of FIG. 3, and is not described further here in the interests of brevity.

In Step U5, the final image from Step U4 is analyzed, e.g. by visual inspection or automated numerical processing. In this example this step corresponds with Step S4 of FIG. 3, and is also not described again in the interests of brevity.

Thus as with the method of FIG. 3, the method of FIG. 5 results in a single final image that may in effect be treated as if it were a single conventional digital fluorescence microscopy image for further analysis, but which incorporates features from images for a range of focal plane depths and exposure times. (As an aside, it may be noted the method of FIG. 5 reduces to the method of FIG. 3 for the case the subset of images selected at Step U2 of FIG. 5 comprises only one image per Z-stack/exposure time, namely the single best focus image.)

It will again be appreciated there are various modifications that could be made to the method described with reference to FIGS. 5 and 6. For example, different characteristic "quality-of-focus" and "contrast" measurements may be defined, e.g. based on the many different ways of numerically defining such image characteristics that are well known from general image processing techniques.

Furthermore, different numbers of original images may be used for different embodiments. For example, more or fewer images per Z-stack may be used depending on the sample thickness and the microscope's depth of focus. Similarly, images may be obtained for more or fewer exposure times, and for different ranges of exposure time, depending on the expected range in fluorescence intensity to be imaged. For example, in some cases only two different exposure times may be employed. What is more, it is not necessary to obtain the same number of images for each exposure time, and furthermore still the Z-stacks for each exposure time need not all be taken at the same focal plane depths.

In other examples, Step U2 may be removed so that all images are used in step U3 (such that the method in effect corresponds to the method of FIG. 3 with the intermediate image of Step S2 derived from a MIP of the respective Z-stacks). However, the processing of FIG. 5 based on selecting a subset of good-focus images for further processing can help ensure that only images which have fluorescent material in good focus contribute to the final resultant image. The inventors have found in some cases this can help reduce halos that might otherwise surround fluorescent structures in the final image caused by the contribution of relatively poor focus images. However, in cases where such halos are not considered to be a problem (e.g. because the images in each Z-stack are relatively close together in Z and there are not many of them, or because the microscope optics have a relatively large depth of field), then Step U2 may be left out so that all images are maximum projected at Step U3.

An alternate to the combined processing of Steps U2 and U3 would be to include all original images in the derivation of the intermediate images, but to combine the images from each Z-stack in a weighted manner. For example, the intermediate images may be based on local-contrast weighting of an average of signal values for each pixel location in the Z-stack. That is to say the original images of each Z-stack may be combined together (fused) to form the respective intermediate images in the same way that the different intermediate images of FIGS. 4 and 6 are combined together to form their respective final images.

Still another way to derive the intermediate images would be to determine a characteristic local contrast for each image at each pixel location (e.g. as described above), and then populate the corresponding pixel location in the associated intermediate image with the image signal value associated with the image in the Z-stack having the greatest contrast for that pixel location. This is in effect a variant of the MIP scheme whereby the projected image is not based on the pixels having the greatest signal values, but is based in the pixels having the greatest local contrast. A potential advantage of this approach is that might be expected to provide improved results for a sample that might display fluorescent probe spots at any location in any image. For example, one image plane might have a small number of fluorescent spots in focus, e.g. three, while other image planes might have many more fluorescent spots in focus, e.g. ten times more. With the method of FIG. 5, the image having few spots may be discarded because its relative uniformity may be characterized as poor focusing of structures. This means the information associated with the good-focus spots in this image would be lost. However, by allowing pixels from all images to contribute to the intermediate images based on their local contrasts, information on focused structures in otherwise uniform images can be maintained.

While the above examples have employed intermediate images in the derivation of a final image from the original images, this may not be done in all examples. For example, mathematically identical processing, or simply a modified combination scheme, may mean that the original images can be combined into a final resultant image in a single step. That is to say, the step of deriving the intermediate images may be skipped. What is more, in the above examples the intermediate images represent combinations of images from different focal plane depths for each exposure time. In other embodiments the images may be combined "the other way around". E.g. the intermediate images may be formed by combining images with different exposure times (e.g. using the above-described contrast-based image fusion techniques) for each focal plane depth. These intermediate images from each focal plane depth may then be combined to form the final resultant image, e.g. using MIP.

Figure 7:
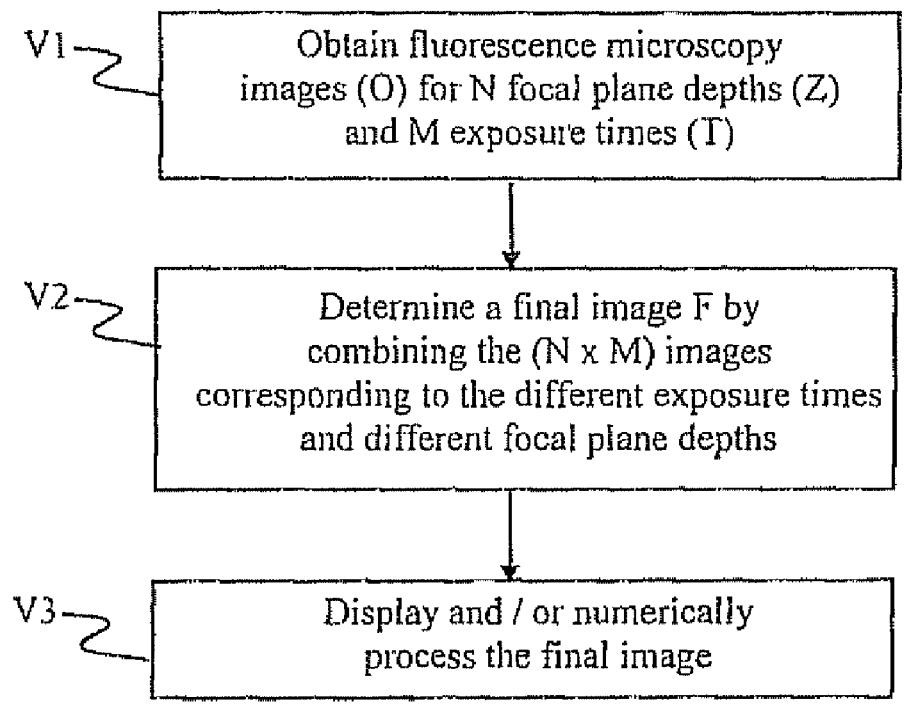
FIG. 7 is a flow diagram representing a scheme for combining digital fluorescence microscopy images obtained for a plurality of different exposure times and different focal plane depths to generate a single resultant image according to yet another embodiment of the invention.

FIG. 7 is flow diagram schematically representing a method for generating a fluorescence microscopy image for subsequent analysis according to another embodiment of the invention. FIG. 8 schematically represents how different fluorescence microscopy images are obtained and combined in accordance with this embodiment of the invention. FIGS. 7 and 8 broadly correspond to, and will be generally understood from, FIGS. 3 and 4 and FIGS. 5 and 6. However, whereas FIGS. 3 and 4 and FIGS. 5 and 6 relate to schemes based on deriving intermediate images, FIGS. 7 and 8 relate to a scheme in which all the original images are combined in a single step.

Step V1 of FIG. 7 is the same as Steps S1 and U1 of FIGS. 3 and 5 respectively (although the actual sample and the staining used may again be different). Thus in Step V1 a series of 24 digital fluorescence microscopy images O are obtained using a conventional digital fluorescence microscope. As above, images are recorded for eight different focal plane depths ($Z_{1,2\ldots8}$), and for three different exposure times ($T_{1,2,3}$) at each depth.

In Step V2 the original images are combined to form a final resultant image. This may be done by simultaneously fusing all original images in the same way that the intermediate images I are fused/combined to provide the resulting final images of the methods of FIGS. 3 and 5, e.g., based on averaging image signal values in each original image for each pixel location with a weighting based on a characteristic measurement of local contrast.

In Step V3, the final image from Step V2 is analyzed, e.g. by visual inspection or automated numerical processing. This step corresponds with Step S4 of FIG. 3, and is not described again.

Thus as with the methods of FIGS. 3 and 4, the method of FIG. 7 results in a single final image that may in effect be treated as if it were a single conventional digital fluorescence microscopy image so far as further analysis is concerned, but which incorporates features from images for a range of focal plane depths and exposure times.

It will be appreciated that the above described methods may be used for processing images obtained using different fluorescent labeling schemes, and the resulting final images for the different labeling schemes compared as might normally be done. For example, processing could be independently applied to respective series of DAPI counter stain, Spectrum Green and Spectrum Orange images for different focal plane depths and exposure times to provide three corresponding final images. These images may then be analyzed/compared according to conventional techniques.

Figure 9:
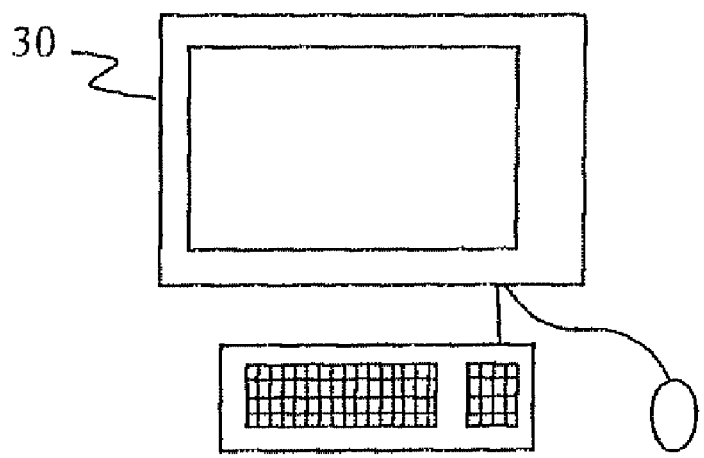
FIG. 9 schematically shows a computer running software for implementing a method according to an embodiment of the invention.

Embodiments of the invention may be implemented in software running on a computer, e.g., an application specific computer, such as might be coupled to a microscope, or a suitably programmed general purpose computer 30 such as shown in FIG. 9. Such a computer may also be incorporated in, or otherwise coupled to, a microscope for obtaining images, e.g. over a dedicated or network connection.

Figure 10:
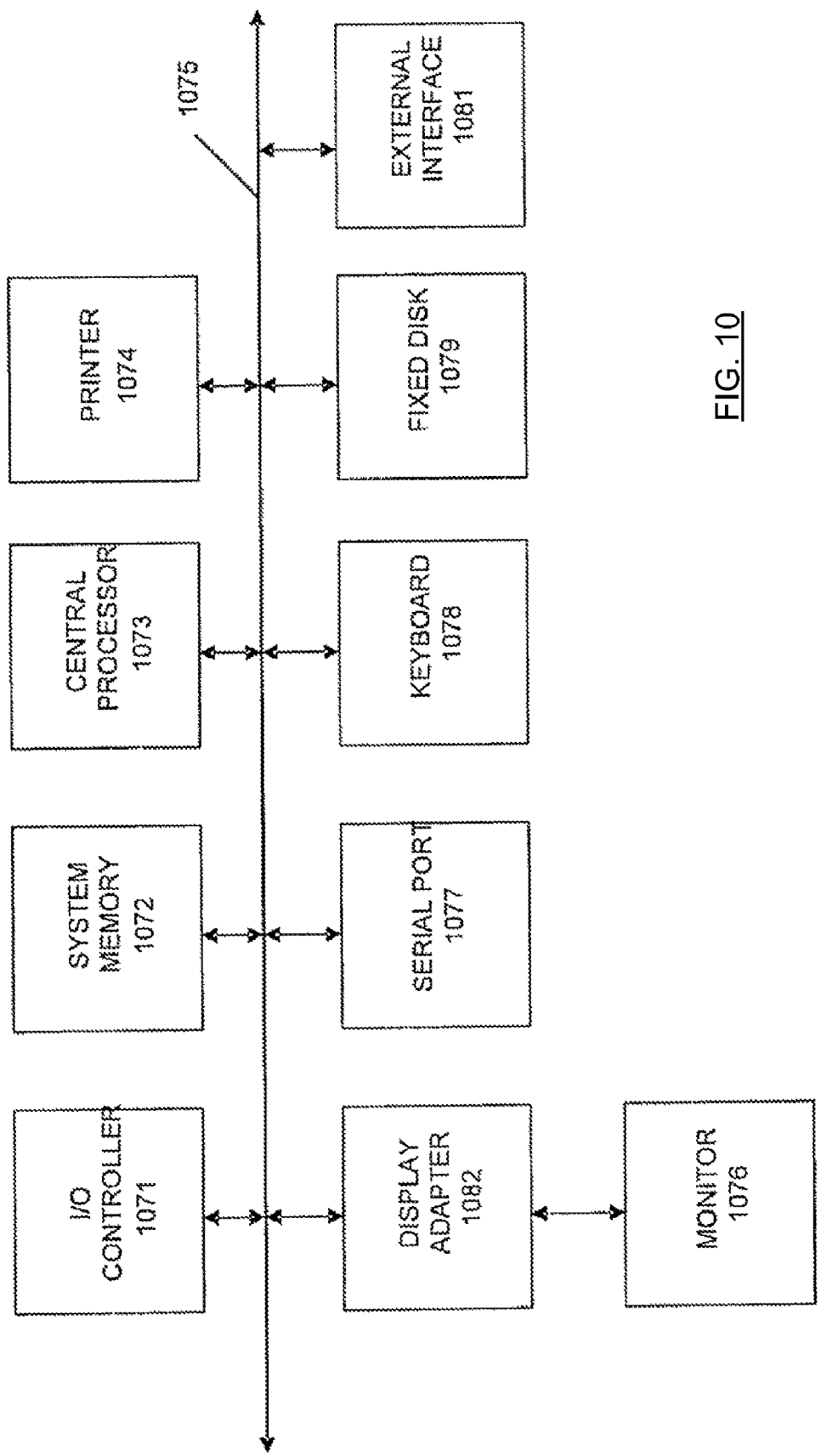
FIG. 10 shows a block diagram of an exemplary computer apparatus/terminal usable with system and methods according to embodiments of the present invention.

FIG. 10 shows a block diagram of an exemplary computer apparatus/terminal usable with system and methods according to embodiments of the present invention. The computer terminal may utilize any suitable number of subsystems. Examples of such subsystems or components are shown in FIG. 10. The subsystems shown in FIG. 10 are interconnected via a system bus 1075. Additional subsystems such as a printer 1074, keyboard 1078, fixed disk 1079, monitor 1076, which is coupled to display adapter 1082, and others are shown. Peripherals and input/output (I/O) devices, which couple to I/O controller 1071, can be connected to the computer system by any number of means known in the art, such as serial port 1077. For example, serial port 1077 or external interface 1081 can be used to connect the computer apparatus to a wide area network such as the Internet, a mouse input device, or a scanner. The interconnection via system bus allows the central processor 1073 to communicate with each subsystem and to control the execution of instructions from system memory 1072 (e.g. RAM) or the fixed disk 1079 (e.g. a magnetic hard drive, flash memory, or an optical disk), as well as the exchange of information between subsystems. The system memory 1072 and/or the fixed disk 1079 may embody a computer readable medium.

Although characteristic contrast measurements have been described here for the image fusion steps, other functions which promote good contrast, good exposure or other useful properties could be employed to produce a resultant image with good contrast, good exposure, other properties, or combination of these properties.

For example, a characteristic measure of how well an image is exposed could be used (instead of local contrast) to weight the signals for different pixel locations during image combination/fusion. Such a measure may be based, for example, on how near the signal values for a given pixel location in each image to be fused (e.g. the intermediate images of FIG. 4) is to the middle of the dynamic range of signal values available in the images. For example, in images with an 8-bit representation of signal values (i.e. 0 to 255), signal values may be weighted according to how near they are to 127. Image signal values near 0 are given less weight because they are likely to be associated with under-exposed regions. Image signal values near 255 are similarly given less weight because they are likely to be associated with over-exposed regions.

Processing in accordance with embodiments of the invention may be employed in any of the many application if fluorescence microscopy imaging. For example, some typical applications might include studies involving the use of fluorescent DNA probes to detect amplifications, deletions or translocations of genes via the presence or absence of fluorescent signals normally appearing as "spots" within a cell nucleus. For example the PathVysion kit produced by Vysis, Inc. may be employed to identify and quantify HER-2/neu gene amplification by fluorescent in situ hybridization where the quantity of amplification indicates whether HERCEPTIN® would be an effective treatment for a breast cancer patient. The kit contains three components—a DAPI counterstain attaches to the cell nucleus; a Spectrum Green DNA "control" probe attaches to centromeric areas on chromosome 17; and a Spectrum Orange DNA probe attaches to the HER-2/neu gene on chromosome 17. The ratio of Spectrum Orange "spots" to Spectrum Green "spots" in a respective final image obtained for each component in accordance with embodiments of the invention may be used to quantify HER-2/neu gene amplification within the nucleus. For example, the number of Spectrum Green spots relate to how many chromosome 17s, there are and the number of Spectrum Orange spots relate to the amount of HER-2/neu gene. A ratio of 1 may be considered normal, whereas a different ratio may indicate amplification.

It will be appreciated that while the above description has focused on fluorescence microscopy imaging application, processing in accordance with embodiments of the invention may also be applied to fluorescence images obtained using other imaging apparatus, e.g. a line scanning device, a conventional camera, a scanner, a cytometry device, a cell imaging platform, high content imaging devices and/or cell separation devices e.g., a flow cytometry device or cell picking device.

Thus there has been described a method for generating a fluorescence image of a sample. The method comprises a step of obtaining a series of fluorescence images of the sample for a plurality of different focal plane depths in the sample and different exposure times, e.g. fluorescent microscopy images. The images may be obtained directly from a microscope, or from a library of images. Images comprising the series of fluorescence images are combined to form a single resultant fluorescence image of the sample. The single resultant image may then be analyzed as if it were a conventional fluorescence image, e.g. by visual inspection or numerical processing. However, because the resultant image is based on images from a range of focal plane depths and exposure times, different structures that appear under only certain conditions (i.e. in only certain images of the original series of fluorescence images) can appear together in a single image, thus simplifying visualization, interpretation and analysis of the sample.

The specific details of the specific aspects of the present invention may be combined in any suitable manner without departing from the spirit and scope of embodiments of the invention. However, other embodiments of the invention may be directed to specific embodiments relating to each individual aspects, or specific combinations of these individual aspects.

It should be understood that the present invention as described above can be implemented in the form of control logic using hardware and/or using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A method for generating an output data set representing a fluorescence image of a sample, the method comprising the steps of:
   (a) obtaining an input data set comprising a plurality of florescence images of the sample, the plurality of fluorescence images representing fluorescence images of the sample for a plurality of different focal plane depths in the sample and different exposure times, wherein the respective ones of the plurality of fluorescence images comprise image signal values for a two-dimensional array of pixel locations; and
   (b) combining, with a processor of a computer, image signal values from different ones of the plurality of fluorescence images from the different focal plane depths and different exposure times to form a two-dimensional output data set representing a single resultant fluorescence image of the sample;
   wherein step (b) comprises the steps of:
   (b1) deriving an intermediate image for each of the different exposure times from the images for the different focal plane depths for the respective different exposure times, and
   (b2) combining the intermediate images for the different exposure times to form the single resultant image; and
   wherein step (b2) comprises determining for each pixel location in the intermediate images a weighted average of the corresponding image signal values in the different intermediate images, and wherein the weightings for each image signal value in the intermediate images are based on a measure of a variation in the image signal values among neighboring pixel locations.

2. The method of claim 1, wherein step (b1) comprises selecting, for each of the different exposure times, one of the images from the different focal plane depths as the derived intermediate image for that exposure time.

3. The method of claim 2, wherein the selection of the image as the derived intermediate image for each exposure time is based on a characteristic quality-of-focus measurement for the images at the different focal plane depths.

4. The method of claim 3, wherein the characteristic quality-of-focus measurement is based on a measure of variations in image signal value among pixels in the respective images.

5. The method of claim 1, wherein the intermediate image for each of the different exposure times is derived by performing a maximum intensity projection analysis of the images for the different focal plane depths for the respective exposure times.

6. The method of claim 1, wherein step (b1) comprises selecting, for each of the different exposure times, a subset of the images from the different focal plane depths for that exposure time, and deriving the intermediate image for each exposure time by combining the corresponding subset of the images.

7. The method of claim 6, wherein the selection of the subset of the images is based on a characteristic quality-of-focus measurement for the images at the different focal plane depths.

8. The method of claim 7, wherein the characteristic quality-of-focus measurement is based on a measure of variations in image signal value among pixels in the respective images.

9. The method of claim 6, wherein the intermediate image for each of the different exposure times is derived by performing a maximum intensity projection analysis of the subset of the images for the respective exposure times.

10. The method of claim 1, further comprising a step of displaying the resulting fluorescence image on a monitor.

11. The method of claim 1, further comprising a step of numerical image processing of the resulting fluorescence image.

12. An apparatus for generating an output data set representing a fluorescence image of a sample, the apparatus comprising:
- a source of an input data set, the input data set comprising a plurality of fluorescence images of the sample, the plurality of fluorescence images representing fluorescence images of the sample obtained for a plurality of different focal plane depths in the sample and different exposure times, wherein the respective ones of the plurality of fluorescence images comprise image signal values for a two-dimensional array of pixel locations; and the apparatus further comprising:
- a processor combining the image signal values from different ones of the plurality of fluorescence images from the different focal plane depths and different exposure times to form a two-dimensional output data set representing a single resultant fluorescence image of the sample;
- wherein combining the image signal values from different ones of the plurality of fluorescence images from the different focal plane depths and different exposure times comprises the steps of:
- (b1) deriving an intermediate image for each of the different exposure times from the images for the different focal plane depths for the respective different exposure times, and
- (b2) combining the intermediate images for the different exposure times to form the single resultant image; and
- wherein step (b2) comprises determining for each pixel location in the intermediate images a weighted average of the corresponding image signal values in the different intermediate images, and wherein the weightings for each image signal value in the intermediate images are based on a measure of a variation in the image signal values among neighboring pixel locations.

13. A non-transitory computer program product comprising a computer readable medium storing a plurality of instructions for controlling a processor to perform an operation for generating an output data set representing a fluorescence image of a sample, the instructions comprising:
- (a) obtaining an input data set comprising a plurality of fluorescent images of the sample, the plurality of fluorescence images representing fluorescence images of the sample for a plurality of different focal plane depths in the sample and different exposure times, wherein the respective fluorescence images comprise image signal values for a two-dimensional array of pixel locations; and
- (b) combining, with the processor, image signal values from different ones of the plurality of fluorescence images from the different focal plane depths and different exposure times to form a two-dimensional output data set representing a single resultant fluorescence image of the sample;
- wherein step (b) comprises the steps of:
- (b1) deriving an intermediate image for each of the different exposure times from the images for the different focal plane depths for the respective different exposure times, and
- (b2) combining the intermediate images for the different exposure times to form the single resultant image; and
- wherein step (b2) comprises determining for each pixel location in the intermediate images a weighted average of the corresponding image signal values in the different intermediate images, and wherein the weightings for each image signal value in the intermediate images are based on a measure of a variation in the image signal values among neighboring pixel locations.

* * * * *